United States Patent
Willson (10) Patent No.: US 6,207,716 B1
(45) Date of Patent: *Mar. 27, 2001

(54) NON-STEROIDAL LIGANDS FOR THE ESTROGEN RECEPTOR

(75) Inventor: Timothy Mark Willson, Durham, NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/182,244

(22) Filed: Oct. 30, 1998

Related U.S. Application Data (60) Continuation of application No. 08/877,665, filed on Jun. 18, 1997, now Pat. No. 5,877,219, which is a division of application No. 08/232,910, filed on Apr. 25, 1994, now Pat. No. 5,681,835.

(51) Int. Cl.[7] ................ A61K 31/165; C07C 233/00

(52) U.S. Cl. ............... 514/617; 564/74; 564/181; 564/265; 564/305; 514/237.5; 514/364; 514/599; 514/520; 514/532; 514/570; 514/640; 514/648; 514/617; 514/726; 544/176; 548/131; 558/401; 560/101; 562/491

(58) Field of Search ................ 514/237.5, 364, 514/599, 520, 532, 570, 640, 648, 617, 726; 558/401; 544/176; 548/131; 560/101; 562/491; 564/74, 265, 305, 181, 809

(56) References Cited

U.S. PATENT DOCUMENTS 5,681,835 * 10/1997 Willson ............... 514/237.5
5,877,219 * 3/1999 Willson ............... 514/617

* cited by examiner

Primary Examiner—Shailendra Kumar
(74) Attorney, Agent, or Firm—Nixon & Vanderhye P.C.

(57) ABSTRACT

Novel non-steroidal ligands for the estrogen receptor which possess tissue-dependent estrogenic and antiestrogenic activity as well as methods for making the same and their applications in treating a variety of disease states.

19 Claims, 1 Drawing Sheet

NON-STEROIDAL LIGANDS FOR THE ESTROGEN RECEPTOR

This is a continuation of application Ser. No. 08/877,665, filed Jun. 18, 1997, now U.S. Pat. No. 5,877,219, which is a divisional of application Ser. No. 08/232,910, filed Apr. 25, 1994, now U.S. Pat. No. 5,681,835.

FIELD OF INVENTION

The present invention relates to novel non-steroidal ligands for the estrogen receptor which possess tissue-dependent estrogenic and antiestrogenic activity as well as methods for making the same and their applications in treating a variety of disease states.

BACKGROUND OF THE INVENTION

Estrogens are an important class of steroidal hormones that stimulate the development and maintenance of fundamental sexual characteristics in humans. In the past, estrogens have been found useful in the treatment of certain medical conditions and diseases. For example, estradiol, a steroid hormone produced by the ovary, is useful in the treatment of osteoporosis, cardiovascular disease, premenstrual syndrome, vasomotor symptoms associated with menopause, atrophic vagginitis, Kraurosis vulvae, female hypogonadism, primary ovarian failure, excessive hair growth and prostatic cancer. Unfortunately, administration of such steroids have been associated with a number of side effects, including myocardial infarction, thromboembolism, cerebrovascular disease, and endometrial carcinoma.

For example, hormone replacement therapy (HRT) with estrogen has been determined to be a clinically effective treatment for osteoporosis in post-menopausal women, however less than 15% of eligible women are currently prescribed HRT despite clinical trials that have demonstrated a 50% reduction in hip fractures and a 30% reduction in cardiovascular disease. Non-compliance arises from patient and physician concerns over the two fold increased risk of endometrial cancer observed with HRT employing estrogen alone as well as the association between estrogen therapy and breast cancer. Although unproven in the clinic, this suspected risk for breast cancer has led to HRT being contra-indicated in a significant percentage of post-menopausal women. Co-therapy with progestins has been shown to protect the uterus against cancer while maintaining the osteoprotective effects of the estrogen, however the progestin introduces other side-effects such as withdrawal bleeding, breast pain and mood swings.

In light of problems associated with estrogen therapy, a significant amount of research has been carried out to identify effective nonsteroidal estrogen and antiestrogenic compounds. In general, such compounds may be characterized as both estrogenic and antiestrogenic because while they all bind to the estrogen receptor, they may induce an estrogenic or antiestrogenic effect depending upon the location of the receptor. In the past, it has been postulated that the binding of various nonsteroidal estrogen and antiestrogenic compounds to the estrogen receptor was due to the presence of a common pharmacophore (shown below in Scheme A) which was recurrent in the chemical structures of these compounds.

Scheme A or

This pharmacophore later became the structural backbone around which nonsteroidal estrogen and antiestrogenic compounds were constructed. Its presence in the constructs of various compounds such as hexestrol, tamoxifen, chroman, triphenylethylene, DES, clomiphene, centchroman, nafoxidene, trioxifene, toremifene, zindoxifene, raloxifene, droloxifene, DABP, TAT-59 and other structurally related compounds has become accepted in the art as the molecular key to estrogen receptor binding specificity.

An example of one noteworthy nonsteroidal antiestrogen is tamoxifen (TAM), (Z)-1,2-diphenyl-1-[4-[2-(dimethylamino)ethoxy]phenyl]-1-butene, which is a triphenylethylene derivative. Tamoxifen effectively antagonizes the growth-promoting effect of estrogens in primary target tissues such as the breast and ovum.

Currently, this non-steroidal estrogen as well as a structurally similar compound known as raloxifene have been developed for the treatment and/or prevention of osteoporosis, cardiovascular disease and breast cancer in addition to the treatment and/or prevention of a variety of other disease states. Both compounds have been shown to exhibit an osteoprotective effect on bone mineral density combined with a positive effect on plasma cholesterol levels and a greatly reduced incidence of breast and uterine cancer. Unfortunately, tamoxifen and raloxifene both have unacceptable levels of life-threatening side effects such as endometrial cancer and hepatocellular carcinoma.

Accordingly, it would be advantageous to develop a series of non-steroidal compounds which retain beneficial characteristics such as osteoprotective activity while minimizing any undesirable side effects. While it is presently accepted that the pharmacophore backbone mentioned above is responsible for estrogen receptor binding specificity, it has now been discovered that certain novel estrogen binding ligands can be constructed as set forth herein which incorporate particular moieties onto such pharmacophore-based compounds, thereby maximizing beneficial characteristics such as osteoprotective function while minimizing undesireable characteristics such as an increased risk of cancer.

SUMMARY OF THE INVENTION

The present invention comprises the genus of compounds represented by Formula (I):

FORMULA I wherein $R^1-R^4$ are defined hereinafter. Also part of the present invention are pharmaceutical compositions comprising one or more of the compounds of Formula (I) as well as their use, methods for their preparation and intermediates involved in the synthesis of the same.

DETAILED DESCRIPTION OF THE INVENTION

The present invention comprises the genus of compounds represented by Formula (I):

wherein
$R^1$ is —$(CH_2)_nCR^5$=$CR^6R^7$; —$(CH_2)_mC(X)NR^8R^9$; or $R^2$ and $R^3$ are independently H, —$CH_3$, —OH, —$OCH_3$, —$OCH_2CH_3$ or —$CH(CH_3)_2$;

$R^4$ is —CN, —$NO_2$, —$CH_3$, —$CH_2CH_3$, —$CH_2CH_2$—Y or —Y;

$R^5$ and $R^6$ are independently H, —$C_{1-4}$alkyl, —$C_{2-4}$alkenyl, —$C_{2-4}$alkynyl, —X—$C_{1-3}$alkyl, —X—$C_{2-4}$alkenyl, —X—$C_{2-4}$alkynyl or —Y;

$R^7$ is —CN, —$C_{1-4}$alkyl—OH, —$C(O)O(CH_3)_3$, —$C(O)NR^{10}R^{11}$, —$C(O)NR^{12}R^{13}$, —$C_{1-4}$alkyl—$NR^{10}R^{11}$, —$C(O)R^{12}$, —$C(O)OR^{12}$, —$C(O)NR^{12}OR^{13}$, —$C(O)NHC(O)R^{12}$, —$C(O)NHCH_2R^{12}$, —$C(NH_2)(NOR^{12})$, —$S(O)R^{12}$, —$S(O)(O)(OR^{12})$, —$S(O)(O)(NHCO_2R^{12})$, $PO_3R^{12}$, —$P(O)(NR^{12}R^{13})(NR^{12}R^{13})$, —$P(O)(NR^{12}R^{13})(OR^{14})$, —$CONR^{12}(CH_2)_q$ $OCH_3$, —$CONR^{12}(CH_2)_qNR^8R^9$ or oxadizole substituted with methyl;

$R^8$ and $R^9$ are independently hydrogen, —$C_{1-7}$alkyl, —$C_{3-7}$cycloalkyl, —O—$C_{1-7}$alkyl, —$C_{1-7}$alkyl—Y or phenyl;

$R^{10}$ and $R^{11}$ are independently methyl or ethyl or, taken together form a morpholino group bonded via its nitrogen atom;

$R^{12}$, $R^{13}$ and $R^{14}$ are independently H, —$C_{1-12}$alkyl, —$C_{2-12}$alkenyl, —$C_{2-12}$alkynyl, —O—C1-12alkyl, —O—$C_{2-12}$alkenyl, —O—$C_{2-12}$alkynyl, —$C_{3-7}$cycloalkyl, —$C_{3-7}$cycloalkenyl, linear and cyclic heteroalkyl, aryl, heteroaryl or —Y;

X is oxygen or sulfur;

Y is a halogen;

n is an integer selected from 0, 1 or 2;

m is the integer 1 or 2;

p is an integer selected from 1 to 4; and q is an integer from 1–12.

As provided herein, the term "alkyl", alone or in combination, is defined herein to be straight chain or branched chain saturated hydrocarbon groups from $C_1$ to $C_7$ unless otherwise preceeded by some other chain length designator. The term "lower alkyl" is defined herein as $C_1$ to $C_4$ unless otherwise preceeded by some other chain length designator. Exemplary alkyl groups include methyl, ethyl, n-propyl, isopropyl, isobutyl, n-butyl, n-hexyl, and the like.

The term "haloalkyl" is defined herein as an alkyl substituted with one or more halogens. The term "cycloalkyl" is defined herein to include cyclic hydrocarbon radicals from $C_3$–$C_7$. Some exemplary cycloalkyl radicals include cyclopropyl, cyclobutyl, cyclobutyl, and cyclopentyl.

The term "aryl", alone or in combination, is defined herein as a monocyclic or polycyclic group, preferably a monocyclic or bicyclic group, i.e. phenyl or naphthyl, which can be unsubstituted or substituted, for example, with one or more and, in particular, one to three substituents selected from halogen, alkyl, hydroxy, alkoxy, haloalkyl, nitro, amino, acylamino, alkylthio, alkylsulfinyl and alkylsulfonyl. Some exemplary aryl groups include phenyl, 2-chlorophenyl, 3-chlorophenyl, 4-chlorophenyl, 2-methylphenyl, 4-methoxyphenyl, 3trifluoromethylphenyl, 4-nitrophenyl, and the like.

The term "heteroaryl" is defined herein as a 5-membered or 6-membered heterocyclic aromatic group which can optionally carry a fused benzene ring and which can be unsubstituted or substituted, for example, with one or more and, in particular, one to three substituents selected from halogen, alkyl, hydroxy, alkoxy, haloalkyl, nitro, amino, acylamino, alkylthio, alkylsulfinyl and alkylsulfonyl.

The term "halogen" is defined herein to include fluorine, chlorine, bromine and iodine.

The terms "linear and cyclic heteroalkyl" are defined in accordance with the term "alkyl" with the suitable replacement of carbon atoms with some other atom such as nitrogen or sulphur which would render a chemically stable species.

Additionally, the functional groups mentioned above have been set forth with parenthetical designations "( )" surrounding certain atoms or groups of atoms where it seemed desireable to elucidate molecular structure or bonding schemes. In particular, a single atom such as "O" or a group of atoms such as "$NH_2$" may be presented in parentheses within the formula of one of the functional groups set forth above [see, for example, when $R^7$ is . . . —$C(O)R^{12}$, —$C(O)OR^{12}$, —$C(O)NR^{12}OR^{13}$, —$C(NH_2)(NOR^{12})$, etc.] In such a situation, the parentheses are intended to illustrate that the atom or groups of atoms contained therein are bonded to the nearest preceeding chemically suitable atom which is not surrounded by parentheses.

More particularly, for example, —C(O)R$^{12}$ is intended to represent a functional group wherein the oxygen is bonded to the carbon, the nearest preceeding atom which is not surrounded by parentheses and is chemically suited for bonding according to classical orbital electron bonding theory. Alternatively, —C(NH$_2$)(NOR$^{12}$) is intended to represent a functional group wherein the nitrogen present in both NH$_2$ and NOR$^{12}$ is bonded to the carbon, the nearest preceeding atom which is not surrounded by parentheses. These examples are illustrated in (a) and (b) below. Those skilled in the art will recognize that the appropriate bonding schemes (e.g. single, double, etc) are evident from the rules of orbital bonding.

Additionally, some of the functional groups mentioned above have been set forth with parenthetical designations "( )" surrounding certain atoms or groups of atoms wherein the parentheses are immediately followed with an alphabetical or numerical subscript [see, for example, when R$^7$ is . . . —CONR$^{12}$(CH$_2$)$_q$OCH$_3$]. In such a situation, it is intended that the atom or groups of atoms contained therein are present within the functional group as multiples of the subscript. For example, if q=2 when R$^7$ is —CONR$^{12}$(CH$_2$)$_q$OCH$_3$, then R$^7$=—CONR$^{12}$CH$_2$CH$_2$OCH$_3$.

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

Some specific compounds of Formula (I) are listed below, the synthesis of which was performed in accordance with the Example section set forth below.

Compound No.
1. 3-[4-(1,2-Diphenyl-but-1-enyl)-phenyl]-N,N-diethyl acrylamide.
2. 3-[4-(1,2-Diphenyl-but-1-enyl)-phenyl]-N,N-diethyl propionamide.
3. 2-[4-(1,2-Diphenyl-but-1-enyl)-phenyl] cyclopropanecarboxylic acid diethylamide.
4. 3-[4-(1,2-Diphenyl-but-1enyl)-phenyl]-N,N-diethyl-2-methyl-acrylamide.
5. 3-[4-(1,2-Diphenyl-but-1-enyl)-phenyl]-but-2-enoic acid diethylamide.
6. 3-[4-(1,2-Diphenyl-but-1-enyl)-phenyl]-acrylic acid methyl ester.
7. 3-[4-(1,2-Diphenyl-but-1-enyl)-phenyl]acrylonitrile.
8. 3-[4-(1,2-Diphenyl-but-1-enyl)-phenyl]-acrylic acid tert-butyl ester.
9. 3-[4-(1,2-Diphenyl-but-1-enyl)-phenyl]-acrylic acid.
10. 3-[4-(1,2-Diphenyl-but-1-enyl)-phenyl]-1-morpholin-4-yl-prop-2-en-1-one.
11. 3-[4-(1,2-Diphenyl-but-1-enyl)-phenyl]-N-(3methoxy-propyl)-acrylamide.
12. N,N-Dicyclohexyl-3-[4-(1,2-diphenyl-but-1-enyl)-phenyl] acrylamide.
13. N-(2-Dimethylamino-ethyl)-3-[4-(1,2-diphenyl-but-1-enyl)-phenyl]-N-ethyl acrylamide.
14. 3-[4-(1,2-Diphenyl-but-1-enyl)-phenyl]-N-methyl-N-octyl acrylamide.
15. 3-[4-(1,2-Diphenyl-but-1-enyl)-phenyl] acrylamide.
16. 3-[4-(1,2-Diphenyl-but-1-enyl)-phenyl]-N-ethyl acrylamide.
17. 1-Amino-3-[4-(1,2-diphenyl-but-1-enyl)-phenyl]-prop-2-ene-1-one oxime.
18. 3-{2-[4-(1,2-Diphenyl-but-1-enyl)-phenyl]-vinyl}5-methyl-[1,2,4]-oxadiazole.
19. 3-[4-(1,2-Diphenyl-but-1-enyl)-phenyl]-prop-2-ene-1-ol.
20. {3-[4-(1,2-Diphenyl-but-1-enyl)-phenyl]-allyl}dimethylamine.
21. 3-[4-(1,2-Diphenyl-but-1-enyl)-phenyl]-N,N-diethyl thioacrylamide.
22. 3-[4-(1,2-Diphenyl-but-1-enyl)-phenyl]-N-(3-hydroxy-propyl)-acrylamide.

Generally, compounds of Formula (I) can be prepared according to the following synthesis schemes. In all of the schemes described below, it is well understood in the art that protecting groups should be employed where necessary in accordance with general principles of chemistry. These protecting groups are removed in the final steps of the synthesis under basic, acidic, or hydrogenolytic conditions which will be readily apparent to those skilled in the art. By employing appropriate manipulation and protection of any chemical functionalities, synthesis of any compounds of the Formula (I) not specifically set forth herein can be accomplished by methods analogous those illustrated in Schemes B–G set forth below as well as the methods described in the Example section.

Generally, the synthesis employed to yield the compounds of the present invention was designed to give access to analogs of the B-ring with the E-configuration of the central tetra-substituted double bond. One method for the preparation of compounds having Formula (I) incorporates Scheme B as set forth below wherein a suitable bromide, such as bromide (b) [e.g. (E)-1-Bromo-2-phenyl-1-(trimethylsilyl)-1-butene], is synthesized in multi-gram quantities from acetylene (a) using the method of Miller (see Miller, R. B.; Al-Hassan, M. I. Stereospecific Synthesis of (Z)-Tamoxifen via Carbometalation of Alkynylsilanes. *J. Org. Chem.* 1985, 50, 2121–2123). The bromide (b) is coupled with a suitable aryl boronic acid, such as (c), under palladium catalysis to yield the desired aldehyde (d) [e.g. (Z)-1,2-Diphenyl-1-(4-formylphenyl)-1-butene], as a single isomer. Bromide (b) and aldehyde (d) are versatile intermediates for the synthesis of B-ring tamoxifen analogs.

Scheme B

As illustrated below in Scheme C, the coupling of bromide (b) with aryl boronic acid (e) gives a,b-unsaturated diethyl amide (g), which is Compound No. 1 as listed above and exemplified below in Example 2. It should be noted that synthesis of this diethyl amide by such route may likely result in a in low yield possibly due to the thermal instability of aryl boronic acid (e). It was also noted during the development of the compounds of the present invention that the identification of diethyl amide (g) as a compound of interest (i.e. Compound No.1: 3-[4-(1,2-Diphenyl-but-1-enyl)-phenyl]-N,N-diethyl acrylamide) dictated the need for a more efficient synthesis for analog preparation. Accordingly, it was found that Horner-Emmons reaction of aldehyde (d) with phosphonate (f) gave diethyl amide (g) in significantly higher yield.

Scheme C

Additionally, Scheme C set forth above illustrates that the a,b-unsaturated diethyl amide (g) can be converted into:

(a). the thioamide (h), [Compound No.21: 3-[4(1,2-Diphenyl-but-1-enyl)-phenyl]-N,N-diethyl thioacrylamide], with Lawesson's Reagent;

(b). the saturated amide (i), [Compound No.2: 3-[4-(1,2-Diphenyl-but-1-enyl)-phenyl]-N,N-diethyl propionamide] by hydrogenation; or (c). the cyclopropyl amide (j), [Compound No.3: 2-[4-(1,2-Diphenyl-but-1-enyl)-phenyl] cyclopropanecarboxylic acid diethylamide] with the Corey Ylide.

Referring to Scheme D set forth below, analogs of diethyl amide (g) incorporating a trisubstituted a,b-unsaturated double bond may be synthesized from a suitable aldehyde, such as (d), or a suitable ketone, such as (n). More particularly, a Horner-Emmons reaction of methyl phosphonate (k) with aldehyde (d) can be employed to give the a-methyl amide (l) [Compound No. 4: 3-[4-(1,2-Diphenyl-but-1-enyl)-phenyl]-N,N-diethyl-2-methyl-acrylamide] as a single isomer and the reaction of phosphonate (f) with ketone (n) may be employed to give a mixture of E and Z-b-methyl amides (o, p) [Compound No. 5: 3-[4-(1,2-Diphenyl-but-1-enyl)-phenyl]-but-2-enoic acid diethylamide—(Z) and (E) isomers] which can be separated by flash chromatography with their relative stereochemistry being assigned by subsequent $^1$H NMR NOE studies.

Scheme D

Referring to Scheme E set forth below, carboxylic acid (r) [Compound No. 9: 3-[4-(1,2-Diphenyl-but-1-enyl)-phenyl]-acrylic acid] can be derived by saponification of methyl ester (q) [Compound No. 6: 3-[4-(1,2-Diphenyl-but-1-enyl)-phenyl]-acrylic acid methyl ester], which, in turn, can be synthesized from condensation of aldehyde (d) with trimethyl phosphonoacetate as exemplified in Scheme D. Scheme E also illustrates how carboxylic acid (r) may be employed as the key intermediate for the synthesis of a diverse series of a,b-unsaturated amides following coupling to a series of linear and cyclic, alkyl and heteroalkyl amines.

Referring to Scheme F set forth below, oxadiazole (v) [Compound No. 18: 3-{2-[4-(1,2-Diphenyl-but-1-enyl)-phenyl]-vinyl}-5methyl-[1,2,4]-oxadiazole] may be synthesized from nitrile (t) [Compound No. 7: 3-[4-(1,2-Diphenyl-but-1-enyl)-phenyl]-acrylonitrile] by reaction with hydroxylamine to give amide oxime (u) [Compound No. 18: 3-{2-[4-(1,2-Diphenyl-but-1-enyl)-phenyl]-vinyl}-5-methyl-[1,2,4]-oxadiazole] followed by cyclization with acetic anhydride.

Referring to Scheme G as set forth below, alcohol (x) [Compound No. 19: 3-[4-(1,2-Diphenyl-but-1-enyl)-phenyl]-prop-2-ene-1-ol] and dimethyl amine (y) [Compound No.20: {3-[4-(1,2-Diphenyl-but-1-enyl)-phenyl]-allyl}-dimethylamine] may be synthesized from t-butyl ester (w) [Compound No. 8: 3-[4-(1,2-Diphenyl-but-1-enyl)-phenyl]-acrylic acid tert-butyl ester] by hydride reduction followed by mesylation and alkylation with dimethyl amine.

GENERAL PROCEDURES

Unless otherwise noted all starting materials were obtained from commercial suppliers and used without further purification. Melting points were determined in capillary tubes on a Mel-Temp apparatus and are uncorrected. $^1$H NMR and $^{13}$C NMR spectra were obtained on Varian Unity-300 and Varian XRL-300 spectrometers with TMS as an internal standard in CDCl$_3$. Chemical shifts are given in ppm (s); multiplicities are indicated by s (singlet), d (doublet), t (triplet), q (quartet), m (multiplet), br (broadened). Coupling constants (J) are reported in Hz. Microanalyses were performed at Atlantic Microlabs, Inc.

and all values were within ±0.4% of the theoretical values. Mass spectra were recorded on a JEOL JMS-AX505HA Mass Spectrometer with Fast Atom Bombardment ionization. Infrared spectra were recorded on a Perkin-Elmer 1280 Infrared Spectrometer. Analytical thin-layer chromatography was performed on EM Science silica 60 $F_{254}$ glass coated plates, and visualization was accomplished by UV light, iodine, or ammonium molybdate. Flash chromatography was performed with EM Science 230-400 mesh silica gel. MPLC was performed on a Pharmacia LKB Series system using a Rainin Dynamax UV-C detector and a Merck Lobar Si60 (40–63 mm) silica gel column. HPLC was performed on a Shimadzu LC-6A Series HPLC using either a Rainin Dynamax $C_{18}$ RP column or a Rainin Dynamax Silica column. All solvents were of reagent grade and used without further purification. (E)-1-Bromo-2-phenyl-1-(trimethylsilyl)-1-butene [see (b),Scheme B, supra] was prepared by the method of Miller as referenced above and 4-formylboronic acid was prepared by the method of Nöth (see Feulner, H.; Linti, G.; Nöth, H. Preparation and Structural Characterization of p-Formylbenzeneboronic Acid. *Chem. Ber.* 1990, 123, 1841–1843. Boronic acids [see (e) and (m), Schemes C and D, respectively] were prepared at Glaxo Group Research Ltd., Hertfordshire, UK from 3-(4-Bromophenyl)-N,N-diethylacrylamide and 4-Bromoacetophenone respectively using the method of Gilman (see Gilman, H.; Santucci, L; Swayampati, D. R.; Ranck, R. O. Hydroxybenzeneboronic Acids and Anhydrides. *J. Am. Chem. Soc.* 1957, 79, 3077–3082.

EXAMPLES

The following compounds were prepared according to the general synthesis procedures set forth above and are provided herein to better illustrate the how to make various compounds of the present invention. The following Examples are illustrative and not intended to limit the scope of the present invention .

Example 1

(Z)-1,2-Diphenyl-1-(4-formylphenyl)-1-butene

A solution of 1.0 g (3.5 mmol) of (E)-1-Bromo-2-phenyl-1-(trimethylsilyl)-1-butene, 625 mg (4.2 mmol, 1.2 equiv) of boronic acid [see (c), Scheme B] and 400 mg (0.35 mmol, 0.1 equiv) of Pd(PPh$_3$)$_4$ in 10 mL of DME was treated with 2 mL of 2 N Na$_2$CO$_3$ and then refluxed for 6 h. The solution was cooled to RT, poured into NaHCO$_3$ (40 mL), extracted with ethyl acetate (2×40 mL), dried (MgSO$_4$), and the solvent was removed in vacuo. Purification by silica gel flash chromatography using hexane/ethyl acetate 20/1 as eluent afforded 700 mg (69%) of the desired compound named above as a yellow solid: $^1$H NMR (CDCl$_3$, 300 MHz) s 9.82 (s, 1 H), 7.55–7.00 (m, 14 H), 2.48 (q, 2 H), 0.97 (t, 3 H); low resolution MS m/e 313 (MH$^+$). [see, for example (d), Scheme B, supra].

Example 2

3-[4-(1,2-Diphenyl-but-1-enyl)-phenyl]-N,N-diethyl acrylamide

Procedure A A solution of 51 mg (0.18 mmol, 1.1 equiv) of (E)-1-Bromo-2-phenyl-1-(trimethylsilyl)-1-butene, 40 mg (0.16 mmol) of an aryl boronic acid [see (e), Scheme C], and 20 mg (16.2 mmol, 0.1 equiv) of Pd(PPh$_3$)$_4$ in 5 mL of DME was treated with 0.5 mL of 2 N Na$_2$CO$_3$ and then refluxed for 2 h. The solution was cooled to RT, poured into NaHCO$_3$ (20 mL), extracted with ethyl acetate (2×20 mL), dried (MgSO$_4$), and the solvent was removed in vacuo. Purification by silica gel flash chromatography using hexane/ethyl acetate 3/1 as eluent afforded 10 mg (15%) of the desired compound named above as a white solid: m.p. 138–140° C.; $^1$H NMR (CDCl$_3$, 300 MHz) s 7.53 (d, 1 H, J=15.4), 7.38–7.11 (m, 12 H), 6.86 (d, 2 H, J=8.3), 6.66 (d, 1 H, J=15.4), 3.40 (m, 4 H), 2.47 (q, 2 H, J=7.3), 1.19 (m, 6 H), 0.93 (t, 3 H, J=7.3); High Resolution MS Calc. 410.2483, Found 410.2484.

Procedure B Use of Diethyl Diethylcarbamoylmethylenephosphonate [see (f), Scheme C] as stated in the general procedure for Horner-Emmons coupling (see Example 7, infra) with the aldehyde, (Z)-1,2-Diphenyl-1-(4-formylphenyl)-1-butene, followed by purification using silica gel flash chromatography using a gradient of hexane/ethyl acetate 20/1 to 2/1 as eluent afforded 110 mg (42%) of the desired compound named above as a white solid: m.p. 137–138° C.; $^1$H NMR (CDCl$_3$, 300 MHz) s 7.53 (d, 1 H, J=15.4), 7.36–7.11 (m, 12 H), 6.86 (d, 2 H, J=8.3), 6.66 (d, 1 H, J=15.4), 3.42 (m, 4 H), 2.47 (q, 2 H, J=7.3), 1.19 (m, 6 H), 0.93 (t, 3 H, J=7.3); Anal. (C$_{29}$H$_{31}$NO) C, H, N. [see, for example (g), Scheme C, supra].

Example 3

3-[4-(1,2-Diphenyl-but-1-enyl)-phenyl]-N,N-diethyl thioacrylamide

A mixture of 65 mg (0.16 mmol) of 3-[4-(1,2-Diphenyl-but-1-enyl)-phenyl]-N,N-diethyl acrylamide (see Example 2) and 39 mg (95.2 mmol, 0.6 equiv) of Lawesson's reagent were heated in 2 mL dry toluene at 85° C. for 2 h. The solution was cooled to RT and placed directly on a silica gel flash chromatography column. Purification by elution with hexane/ethyl acetate 10/1 afforded 54 mg (83%) of thioamide of the desired compound named above as a yellow foam: m.p. 43–61° C.; $^1$H NMR (CDCl$_3$, 300 MHz) s 7.85 (d, 0.5 H), 7.75 (d, 0.5 H), 7.65 (d, 0.5 H), 7.40–6.80 (m, 13.5 H), 4.05 (m, 2 H), 3.70 (m, 2 H), 2.45 (m, 2 H), 1.30 (m, 6 H), 0.95 (m, 3 H); $^{13}$C NMR (CDCl$_3$, 75 MHz) s 193.83, 144.56, 143.96, 143.18, 143.11, 141.92, 138.26, 133.00, 131.22, 130.83, 129.66, 128.28, 128.01, 127.91, 127.86, 127.70, 127.48, 127.02, 126.83, 126.45, 124.04, 48.54, 46.40, 29.19, 13.86, 13.67, 13.62, 11.66; IR (CHCl$_3$) 3050, 1520, 1210, 950, 750; Anal. (C$_{29}$H$_{31}$NS) C, H, N. [see, for example (h), Scheme C, supra].

Example 4

3-[4-(1,2-Diphenyl-but-1-enyl)-phenyl]-N,N-diethyl propionamide

A solution of 50 mg (0.12 mmol) of 3-[4-(1,2-Diphenyl-but-1-enyl)-phenyl]-N,N-diethyl acrylamide (see Example 2) and 3 mg of tris(triphenylphosphine)-rhodium(I) chloride (Wilkinson's catalyst) in 1 mL dry toluene was stirred over an atmosphere of H$_2$ gas at 50° C. for 16 h. The solution was cooled to RT and the toluene removed in vacuo. Purification of the residue by silica gel flash chromatography using hexane/ethyl acetate 2/1 as eluent afforded 48 mg (95%) of the desired compound named above as a clear, colorless oil: $^1$H NMR (CDCl$_3$, 300 MHz) s 7.37–7.11 (m, 10 H), 6.85 (d, 2 H, J=8.3), 6.78 (d, 2 H, J=8.3), 3.31 (q, 2 H, J=7.1), 3.08 (q, 2 H, J=7.3), 2.81 (t, 2 H, J=8.3), 2.44 (m, 4 H), 1.03 (m, 6 H), 0.91 (t, 3 H, J=7.3); low resolution MS m/e 412 (MH$^+$); Anal. (C$_{29}$H$_{33}$NO) C, H, N. [see, for example (i), Scheme C, supra].

Example 5

2-[4-(1,2-Diphenyl-but-1-enyl)-phenyl] cyclopropanecarboxylic acid diethylamide A solution of 12 mg (0.24 mmol, 2.0 equiv) of sodium hydride (50% in oil) and 54 mg (0.24 mmol, 2.0 equiv) of trimethyloxosulfonium iodide in 2 mL dry dimethyl sulfoxide was stirred 30 min at RT, at which time gas evolution had ceased to occur. A solution of 50 mg (0.12 mmol) of the amide as prepared in Example 2 in 0.5 mL dimethyl sulfoxide was then added and the resulting solution heated to 50° C. for 16 h. The reaction mixture was cooled to RT, poured into 20 mL $H_2O$, and extracted with ethyl acetate (2×20 mL). The organic layers were combined, dried ($MgSO_4$), and the solvent removed in vacuo. Purification of the residue by silica gel MPLC using hexane/ethyl acetate 4/1 as eluent afforded 32 mg (62%) of the desired compound named above as a white solid: m.p. 42–44° C.; $^1$H NMR ($CDCl_3$, 300 MHz) s 7.37–7.10 (m, 10 H), 6.76 (m, 4 H), 3.38 (q, 4 H, J=7.1), 2.45 (q, 2 H, J=7.4), 2.30 (m, 1 H), 1.79 (m, 1 H), 1.55 (m, 1 H), 1.11 (m, 7 H), 0.92 (t, 3 H, J=7.4); low resolution MS m/e 424 ($MH^+$); Anal. ($C_{30}H_{33}NO$) C, H, N. [see, for example (j), Scheme C, supra].

Example 6

(Methyl) Diethyl Diethylcarbamoylmethylenephosphonate

A solution of 4.4 mL (2.2 mmol, 1.1 equiv) of $KN(TMS)_2$ (0.5 M in toluene) was added to a cold (−78° C.) solution of 500 mg (2.0 mmol) Diethyl Diethylcarbamoylmethylenephosphonate in 5 mL dry THF. The resulting solution was stirred 10 min, then 0.15 mL (2.4 mmol, 1.2 equiv) of methyl iodide was added neat. The resulting solution was allowed to warm to RT and stirred 1 h, then poured into brine (70 mL) and extracted with ethyl acetate (2×60 mL). The organic layers were combined, dried ($MgSO_4$), and the solvent removed in vacuo. Purification of the yellow residue via Kügelrohr distillation afforded 525 mg (100%) of the desired compound named above as a clear, colorless oil: b.p. 155° C. at 0.15 torr; $^1$H NMR ($CDCl_3$, 300 MHz) s 4.18 (m, 4 H), 3.60 (m, 1 H), 3.22 (m, 4 H), 1.37 (m, 9 H), 1.18 (m, 6 H). [see, for example (k), Scheme C, supra].

Example 7

General Procedure for Horner-Emmons reactions with (Z)-1,2-Diphenyl-1-(4-formylphenyl)-1-butene. A solution of 1.2 equiv of $KN(TMS)_2$ (0.5 M in toluene) was added to a stirring 0° C. solution of 1.2 equiv. of the appropriate phosphonate in dry THF. The resulting solution was stirred 15 min. at 0° C., then cooled to −78° C. and a solution of (Z)-1,2-Diphenyl-1-(4-formylphenyl)-1-butene in THF was added dropwise. The resulting solution was allowed to warm to RT and stirred 4 h, then warmed to 50° C. for 2 h to ensure reaction completion. The reaction mixture was cooled to RT, poured into brine, and extracted twice with ethyl acetate. The organic layers were combined, dried ($MgSO_4$), the solvent was removed in vacuo, and the residue purified by silica gel flash chromatography.

Example 8

3-[4-(1,2-Diphenyl-but-1-enyl)-phenyl]-N,N-diethyl-2-methyl-acrylamide

Use of (Methyl) Diethyl Diethylcarbamoylmethylenephosphonate as employed above followed by purification via silica gel flash chromatography using hexane/ethyl acetate 3/1 as eluent afforded 36 mg (53%) of of the desired compound named above as a clear colorless oil: $^1$H NMR ($CDCl_3$, 300 MHz) s 7.39–7.11 (m, 10 H), 6.97 (d, 2 H, J=8.0), 6.85 (d, 2 H, J=8.3), 6.32 (s, 1 H), 3.38 (m, 4 H), 2.47 (q, 2 H, J=7.3), 2.00 (s, 3 H), 1.14 (t, 6 H, J=7.1), 0.93 (t, 3 H, J=7.3); low resolution MS m/e 424; Anal. ($C_{30}H_{33}NO$) C, H, N. [see, for example (1), Scheme D, supra].

Example 9

(Z)-and (E)-3-[4-(1,2-Diphenyl-but-1-enyl)-phenyl]-but-2-enoic acid diethylamide Use of Diethyl Diethylcarbamoylmethylenephosphonate as employed above with purification by silica gel flash chromatography using hexane/ethyl acetate 5/2 afforded 95 mg (49%) of the (Z)-isomer of the desired compound named above as a white solid and 11 mg (6%) of the (E)-isomer as a colorless oil. Analytical data for the (Z)-isomer: m.p. 109–111° C.; $^1$H NMR ($CDCl_3$, 300 MHz) s 7.39–7.09 (m, 12 H), 6.85 (d, 2 H, J=8.3), 6.20 (d, 1 H, J=1.0), 3.44 (q, 2 H, J=7.1), 3.33 (q, 2 H, J=7.1), 2.47 (q, 2 H, J=7.5), 2.16 (d, 3 H, J=1.0), 1.13 (m, 6 H), 0.93 (t, 3 H, J=7.6); low resolution MS m/e 424; Anal. ($C_{30}H_{33}NO$) C, H, N. Analytical data for the (E)-isomer: $^1$H NMR ($CDCl_3$, 300 MHz) s 7.36–7.09 (m, 10 H), 7.00 (d, 2 H, J=8.3), 6.81 (d, 2 H, J=8.2), 5.80 (d, 1 H, J=1.0), 3.22 (q, 2H, J=7.2), 2.91 (q, 2 H, J=7.1), 2.45 (q, 2 H, J=7.6), 2.04 (d, 3 H, J=1.0), 0.89 (m, 6 H), 0.74 (t, 3 H, J=7.6); low resolution MS m/e 424. [see, for example (o,p), Scheme D, supra].

Example 10

3-[4-(1,2-Diphenyl-but-1-enyl)-phenyl]-acrylic acid methyl ester

Use of Trimethyl phosphonoacetate as set forth above followed by purification using silica gel flash chromatography using hexane/ethyl acetate 20/1 as eluent afforded 2.33 g (100%) of the desired compound named above as a white solid: m.p. 133–135° C.; $^1$H NMR ($CDCl_3$, 300 MHz) s 7.53 (d, 1 H, J=16.0), 7.39–7.10 (m, 12 H), 6.88 (d, 2 H, J=8.33), 6.27 (d, 1 H, J=16.0), 3.76 (s, 3 H), 2.48 (q, 2 H, J=7.3), 0.93 (t, 3H, J=7.3); low resolution MS m/e 369; Anal. ($C_{26}H_{24}O_2$) C, H, N. [see, or example (q), Scheme E, supra].

Example 11

3-[4-(1,2-Diphenyl-but-1-enyl)-phenyl]-acrylonitrile

Use of Diethyl cyanomethylphosphonate as set forth above with purification by silica gel flash chromatography using hexane/ethyl acetate 10/1 as eluent afforded 125 mg (93%) of the desired compound named above as a clear, colorless oil which solidifies upon standing: m.p. 101–102° C.; $^1$H NMR ($CDCl_3$, 300 MHz) s 7.40–7.07 (m, 13 H), 6.90 (d, 2 H, J=8.6), 5.79 (d, 1 H, J=16.6), 2.48 (q, 2 H, J=7.3), 0.93 (t, 3 H, J=7.3); Anal. ($C_{25}H_{21}N$) C, H, N. [see, for example (t), Scheme F, supra].

Example 12

3-[4-(1,2-Diphenyl-but-1-enyl)-phenyl]-acrylic acid tert-butyl ester

Use of t-butyl diethylphosphonoacetate as set forth above with purification by silica gel flash chromatography using hexane/ethyl acetate 20/1 as eluent then recrystallization from hot hexane afforded 52 mg (95%) of the desired compound named above as a white solid: m.p. 139–140+ C.; $^1$H NMR (CDCl$_3$, 300 MHz) s 7.44–7.09 (m ,13 H), 6.86 (d, 2 H, J=8.3), 6.20 (d, 1 H, J=16.1), 2.47 (q, 2 H, J=7.4), 1.49 (s, 9 H), 0.93 (t, 3 H, J=7.4); low resolution MS m/e 373, no MH$^+$; Anal. (C$_{29}$H$_{30}$O$_2$) C, H. [see, for example (w), Scheme G, supra].

Example 13

1-[4-(1,2-Diphenyl-but-1-enyl)-phenyl]-ethanone

A solution of 172 mg (0.60 mmol) of (E)-1-Bromo-2-phenyl-1-(trimethylsilyl)-1-butene [see (b),Scheme B, supra], 125 mg (0.60 mmol, 1.0 equiv) of boronic acid [see (m), Scheme D] and 70 mg (0.06 mmol, 0.1 equiv) of Pd(PPh$_3$)$_4$ in 8 mL of DME was treated with 0.4 mL of 2 N Na$_2$CO$_3$ and then refluxed for 18 h. The solution was cooled to RT, poured into brine (20 mL), extracted with ethyl acetate (2×20 mL), dried (MgSO$_4$), and the solvent was removed in vacuo. Purification by silica gel flash chromatography using hexane/ethyl acetate 20/1 as eluent afforded 152 mg (78%) of the desired compound named above as a yellow solid: $^1$H NMR (CDCl$_3$, 300 MHz) s 7.6 (d, 2 H), 7.45–7.10 (m, 10 H), 6.98 (d, 2 H), 2.48 (m, 3 H), 0.94 (t, 3-H). [see, for example (n), Scheme D, supra].

Example 14

3-[4-(1,2-Diphenyl-but-1-enyl)-phenyl]-acrylic acid

A solution of 50 mL (16 mmol, 10.0 equiv.) of 0.2 M KOH was added dropwise over 2 minutes to a solution of 600 mg of the ester as prepared in Example 10(1.6 mmol, 1.0 equiv.) in 90 mL of methanol/THF 1/2. The resulting solution was stirred 18 h at RT and the solvent was removed in vacuo. The residue was dissolved in 30 mL of 1M HCl and extracted with ethyl acetate (2×60 mL). The organic layers were combined, dried (MgSO$_4$), and the solvents removed in vacuo. Purification of the residue by silica gel flash chromatography using methylene chloride/methanol 95/5 as eluent provided 370 mg (63%) of the desired compound named above as a white solid: m.p. 148–150° C.; $^1$H NMR (CDCl$_3$, 300 MHz) s 7.60 (d, 1 H, J=15.9), 7.39–7.10 (m, 12 H), 6.89 (d, 2 H, J=8.1), 6.27 (d, 1 H, J=15.9), 2.48 (q, 2 H, J=7.3), 0.93 (t, 3 H, J=7.3); low resolution MS m/e 355; Anal. (C$_{25}$H$_{22}$O$_2$) C, H. [see, for example (r), Scheme E, supra].

Example 15

General Procedure for Coupling Reactions with 3-[4-(1,2-Diphenyl-but-1-enyl)-phenyl]-acrylic acid To a solution of 1.0 equiv of acid (20) in dry methylene chloride was added 1.0 equiv. of EDC, 1.3 equiv. of HOBT and 1.0 equiv. of Et$_3$N followed by 1.2 equiv. of the appropriate amine. The resulting solution was stirred 18 h at RT, then poured into 20 mL of H$_2$O, and extracted twice with ethyl acetate (2×60 mL). The organic layers were combined, washed with H$_2$O (1×20 mL), dried (MgSO$_4$), the solvent was removed in vacuo, and the residue purified by silica gel flash chromatography, silica gel MPLC, or by recrystallization.

Example 16

3-[4-(1,2-Diphenyl-but-1-enyl)-phenyl]-1-morpholin-4-yl-prop-2-en-1-one

Use of morpholine followed by purification by silica gel MPLC using hexane/ethyl acetate 2/1 as eluent followed by recrystallization from hot hexane afforded 12 mg (14%) of the desired compound named above as a white solid: m.p. 150–154° C.; $^1$H NMR (CDCl$_3$, 300 MHz) s 7.53 (d, 1 H, J=15.4), 7.39–7.10 (m, 12 H), 6.87 (d, 2 H, J=8.3), 6.67 (d, 1 H, J=15.4), 3.65 (m, 8 H), 2.48 (q, 2 H, J=7.3), 1.26 (broad, 8 H), 0.93 (t, 3 H, J=7.3); low resolution MS m/e 424; Anal. (C$_{29}$H$_{29}$NO$_2$) C, H, N. [see, for example (s), Scheme E, supra].

Example 17

3-[4-(1,2-Diphenyl-but-1-enyl)-phenyl]-N-(3-methoxy-propyl)-acrylamide

Use of 3-methoxypropylamine followed by purification by recrystallization from hot hexane/ethyl acetate 2/1 followed by silica gel MPLC using hexane/ethyl acetate 1/2 as eluent afforded 20 mg (30%) of the desired compound named above as a white solid: m.p. 132–135° C.; $^1$H NMR (CDCl$_3$, 300 MHz) s 7.43 (d, 1H, J=15.7), 7.36–7.10 (m, 12 H), 7.86 (d, 2 H. J=8.3), 6.20 (d, 1 H. J=15.7), 3.46 (m, 4 H), 3.34 (s,1 H), 2.48 (q, 2 H, J=7.5), 1.80 (m, 2 H), 0.92 (t, 3 H, J=7.5); low resolution MS m/e 426; Anal. (C$_{29}$H$_{31}$NO$_2$) C, H, N. [see, for example (s), Scheme E, supra].

Example 18

N,N-Dicyclohexyl-3-[4-(1,2-diphenyl-but-1-enyl)-phenyl] acrylamide

Use of dicyclohexylamine followed by purification by recrystallization from hot hexane/ethyl acetate 2/1 afforded 29 mg (28%) of the desired compound named above as a white solid: m.p. 194–200° C.; $^1$H NMR (CDCl$_3$, 300 MHz) s 7.43–7.11 (m, 13 H), 6.86 (d, 2 H, J=8.3), 6.69 (d, 1 H, J=15.4), 3.50 (m, 2 H), 2.48 (q, 2 H, J=7.3), 2.25 (m, 2 H), 1.77–1.62 (2 m, 12 H), 1.30–1.10 (m, 8 H), 0.93 (t, 3 H, J=7.3); low resolution MS m/e 518; Anal. (C$_{37}$H$_{43}$NO) C, H, N. [see, for example (s), Scheme E, supra].

Example 19

N-(2-Dimethylamino-ethyl)-3-[4-(1,2-diphenyl-but-1-enyl)-phenyl]-N-ethyl acrylamide hydrogen oxalate Use of 2-dimethylaminoethylamine followed by purification by silica gel flash chromatography using methylene chloride/methanol 15/1 as eluent followed by formation of the hydrogen oxalate salt with 1.1 equiv. of oxalic acid in Et$_2$O afforded 58 mg (53%) of the desired compound named above as a white solid: m.p. 145–147° C.; $^1$H NMR (CDCl$_3$, 300 MHz) s 7.51 (d, 1 H, J=15.1), 7.38–7.10 (m, 12 H), 6.88 (d, 2 H), 6.60 (d, 1 H, J=15.1), 6.12 (m, 2 H), 3.70 (m, 2 H), 3.47 (m, 3 H), 3.35 (m, 2 H), 2.90 (m, 4 H), 2.48 (q, 2 H, J=7.4), 1.20 (m, 2 H), 0.93 (t, 3 H, J=7.4); low resolution MS m/e 453; Anal. (C$_{31}$H$_{36}$N$_2$O C$_2$H$_2$O$_4$) C, H, N. [see, for example (s), Scheme E, supra].

Example 20

3-[4-(1,2-Diphenyl-but-1-enyl)phenyl]-N-(3-hydroxy-propyl)-acylamide

Use of 3-hydroxypropylamine followed by purification by silica gel MPLC using a gradient of hexane/ethyl acetate 2/1 to 100% ethyl acetate as eluent followed by recrystallization from hot hexane afforded 14 mg (15%) of the desired compound named above as a white solid: m.p. 144–146° C.; $^1$H NMR (CDCl$_3$, 300 MHz) s 7.47 (d, 1 H, J=15.6), 7.36–7.10 (m, 12 H), 7.86 (d, 2 H, J=8.3), 6.22 (d, 1 H, J=15.6), 3.62 (m, 2 H), 3.51 (m, 2 H), 3.25 (t, 1 H), 2.47 (q, 2 H, J=7.3), 1.71 (m, 2 H), 0.94 (t, 3 H, J=7.3); low resolution MS m/e 412; Anal. ($C_{28}H_{29}NO_2$) C, H, N. [see, for example (s), Scheme E, supra].

Example 21

3-[4-(1,2-Diphenyl-but-1-enyl)-phenyl]-N-methyl-N-octyl acrylamide

Use of N-methyl-N-octylamine followed by purification by silica gel MPLC using hexane/ethyl acetate 3/1 as eluent afforded 56 mg (41%) of the desired compound named above as a white solid: m.p. 108–109° C.; $^1$H NMR (CDCl$_3$, 300 MHz) s 7.52 (d, 1 H, J=15.4), 7.38–7.14 (m, 12 H), 6.86 (d, 2 H, J=7.8), 6.68 (dd, 1 H, J=15.4), 3.00 (d, 4 H), 2.48 (q, 2 H, J=7.3), 1.26 (m, 8 H), 0.93 (t, 3 H, J=7.3), 0.86 (m, 6 H); low resolution MS m/e 480; Anal. ($C_{34}H_{41}NO$) C, H, N. [see, for example (s), Scheme E, supra].

Example 22

3-[4-(1,2-Diphenyl-but 1-enyl)-phenyl] acrylamide

Use of a saturated solution of ammonia in CH$_2$Cl$_2$ followed by purification by silica gel MPLC using hexane/ethyl acetate 2/1 as eluent afforded 39 mg (39%) of the desired compound named above as a white solid: m.p. 200–202° C.; $^1$H NMR (CDCl$_3$, 300 MHz) s 7.47 (d, 1 H, J=15.6), 7.39–7.10 (m, 12 H), 6.87 (d, 2 H, J=8.3), 6.27 (d, 1 H, J=15.6), 2.48 (q, 2 H, J=7.3), 0.93 (t, 3 H, J=7.3); low resolution MS m/e 354; Anal. ($C_{25}H_{23}NO$) C, H, N.

Example 23

3-[4-(1,2-Diphenyl-but-1-enyl)-phenyl]-N-ethyl acrylamide

A solution of 0.2 mL (0.4 mmol, 1.2 equiv.) of oxalyl chloride (2 M in CH$_2$Cl$_2$) was added to a stirring 0° C. solution of 120 mg (0.3 mmol) of the acid as prepared in Example 14 which was in 2 mL of dry methylene chloride. The resulting solution was allowed to warm to RT and stirred overnight. The solvent was removed in vacuo and the residue dissolved in 2 mL of ether and then added to a rapidly stirring solution of 23 mL of ethylamine (70% wt. in H$_2$O) (0.4 mmol, 1.2 equiv.) in 2 mL of 1M NaOH. The resulting solution was stirred at RT for 2 h. The reaction mixture was poured into ethyl acetate and extracted; the aqueous layer was washed with ethyl acetate (3×10 mL). The organic layers were combined, dried (MgSO$_4$), the solvent was removed in vacuo, and the residue purified by recrystallization from hot ethyl acetate to afford 45 mg (35%) of the desired compound named above as a white solid; m.p. 192–193° C.; $^1$H NMR (CDCl$_3$, 300 MHz) s 7.45 (d, 1 H, J=15.6), 7.39–7.10 (m, 12 H), 6.86 (d, 2 H, J=8.1), 6.20 (d, 1 H, J=15.6), 3.38 (m, 2 H, J=7.3), 2.48 (q, 2 H, J=7.3), 1.17 (t, 3 H, J=7.3), 0.93 (t, 3 H, J=7.3); low resolution MS m/e 382; Anal. ($C_{27}H_{27}NO$) C, H, N. [see, for example (s), Scheme E, supra].

Example 24

1-Amino-3-[4-(1,2-diphenyl-but-1-enyl)-phenyl]-prop-2-ene-1-one oxime

A solution of 1.16 mL (1.16 mmol, 3.1 equiv) of sodium methoxide in methanol (1.0 M) was added to a solution of 78 mg (1.12 mmol, 3.0 equiv) of hydroxylamine hydrochloride in 4 mL dry methanol. The resulting solution was refluxed for 15 min., then cooled to RT. A solution of 125 mg (0.37 mmol) of a nitrile as prepared in Example 11 which was in 2 mL of dry methanol/THF 2/1 was added, and the reaction mixture was refluxed for 16 h. The reaction was cooled, poured into 20 mL brine and extracted with ethyl acetate (2×20 mL), dried (MgSO$_4$), and the solvents were removed in vacuo. Purification by silica gel flash chromatography afforded 61 mg (47%) of the desired compound named above as a white solid: m.p. 182–185° C.; $^1$H NMR (CDCl$_3$, 300 MHz) s 7.38–7.07 (m, 12 H), 6.85 (d, 2 H, J=8.0), 6.68 (d, 1 H, J=16.7), 6.32 (d, 1 H, J=16.7), 4.60 (s, br, 2 H), 2.47 (q, 2 H, J=7.6), 2.17 (s, 1 H), 0.93 (t, 3 H, J=7.6); low resolution MS m/e 369; Anal. ($C_{25}H_{24}N_2O$) C, H, N. [see, for example (u), Scheme F, supra].

Example 25

3-{2-[4-(1,2-Diphenyl-but-1-enyl)-phenyl]-vinyl}-5-methyl-[1,2,4]-oxadiazole

A solution of 60 mg (0.16 mmol) of amide oxime as prepared above in Example 24 which was in 5 mL of acetic anhydride was heated at 80° C. for 18 h, cooled to RT, poured into 10 mL 4 N NaOH and extracted with ethyl acetate (2×20 mL). The organic layers were combined, dried (MgSO$_4$), and the solvent removed in vacuo. The crude material was purified by flash chromatography using hexane/ethyl acetate 10/1 as eluent to afford 21 mg of slightly impure product, which was recrystallized from hot methanol/ethyl acetate 10/1 to give 13 mg (20%) of the desired compound named above as a white crystalline solid: m.p. 158–59° C.; $^1$H NMR (CDCl$_3$, 300 MHz) s 7.50 (d, 1 H, J=16.4), 7.37–7.12 (m, 13 H), 6.87 (m, 2 H), 2.58 (s,3H),2.47 (q,2H, J=7.3), 0.93 (t,3H, J=7.3); low resolution MS m/e 392; Anal. ($C_{27}H_{24}N_2O$) C, H, N. [see, for example (v), Scheme F, supra].

Example 26

3-[4-(1,2-Diphenyl-but-1-enyl)-phenyl]-prop2-ene-1-ol

A solution of 1.35 mL (1.35 mmol, 2.5 equiv) of 1.0 M DIBAL-H in THF was added dropwise to a −78° C. solution of the ester as prepared above in Example 12 which was in 3 mL THF. The resulting solution was stirred 30 min at −78° C. then warmed to RT and stirred 16 h. The excess DIBAL-H was quenched with 1 N HCl and the reaction mixture poured into 20 mL 1 N HCl and extracted with ethyl acetate (2×20 mL). The organic layers were combined, dried (MgSO$_4$), and the solvents removed in vacuo. Purification of the residue by silica gel flash chromatography using hexane/ethyl acetate 5/1 as eluent provided 94 mg (60%) of the desired compound named above as a white solid: m.p. 80–83° C.; $^1$H NMR (CDCl$_3$, 300 MHz) s 7.41–7.02 (m, 12 H), 6.82 (d, 2 H, J=8.3), 6.45 (d, 1 H, J=15.8), 6.23 (d, 1 H, J=5.8, 15.9), 4.24 (m, 2 H), 2.47 (q, 2 H, J=7.6), 1.31 (t, 1 H, J=5.9), 0.93 (t, 3 H, J=7.6); low resolution MS m/e 340; Anal. ($C_{25}H_{24}O$) C, H. [see, for example (x), Scheme G. supra].

Example 27

{3-[4-(1,2-Diphenyl-but-1-enyl)-phenyl]-allyl}-dimethylamine

A solution of 90 mg (0.27 mmol) of the alcohol as prepared above in Example 26 and 41 mg (0.32 mmol, 1.2 equiv) of diisopropylethylamine in 2 mL dry dichloromethane was treated with 33 mg (0.29 mmol, 1.1 equiv) of methanesulfonyl chloride and the resulting solution was stirred at RT for 3 h. The solution was then poured into 10 mL of ethyl acetate and extracted with 10 mL of brine, dried ($MgSO_4$), and the solvents removed in vacuo to provide 108 mg (97%) of a thick golden oil. This material was immediately dissolved in 3 mL dry methanol and then 1-mL of dimethylamine was added. The resulting solution was stirred 16 h at RT then the solvents were removed in vacuo. The residue was dissolved in 10 mL ethyl acetate and extracted with 1 N HCl. The aqueous layer was separated and made basic by addition of 3 N NaOH and then extracted with ethyl acetate (2×10 mL). The basic extracts were combined, dried ($MgSO_4$), and the solvent removed in vacuo. Purification of the residue by silica gel MPLC using dichloromethane/methanol 15/1 as eluent afforded 37 mg (40%) of the desired compound named above as a clear, colorless oil: $^1$H NMR ($CDCl_3$, 300 MHz) s 7.37–7.09 (m, 10 H), 7.02 (d, 2 H, J=8.5), 6.81 (d, 2 H, J=8.1), 6.34 (d, 1 H, J=15.9), 6.14 (dt, 1 H, J=6.6, 15.9), 3.17 (d, 2 H, J=6.6), 2.59–2.42 (m, 6 H), 1.01 (t, 6 H, J=7.3), 0.92 (t, 3 H, J=7.4); low resolution MS m/e 396; Anal. ($C_{29}H_{33}N$) C, H, N. [see, for example (y), Scheme G, supra].

Compounds of Formula (I) which contain acidic moieties may form pharmaceutically acceptable salts with suitable cations. Suitable pharmaceutically acceptable cations include alkali metal (e.g., sodium or potassium) and alkaline earth metal (e.g., calcium or magnesium) cations. In light of the foregoing, any reference to compounds of the present invention appearing herein is intended to include both compounds of Formula (I) as well as pharmaceutically acceptable salts and solvates thereof.

As previously mentioned, the compounds of the present invention are useful for the treatment and/or prevention of a variety of disorders or conditions such as cardiovascular disease, breast cancer, osteoporosis and arthritic conditions. Some other examples of disorders or conditions for which the compounds of the present invention are also useful in treating and/or preventing include premenstrual syndrome, vasomotor symptoms associated with menopause, atrophic vagginitis, Kraurosis vulvae, female hypogonadism, primary ovarian failure, excessive hair growth and prostatic cancer.

It will be appreciated by those skilled in the art that reference herein to treatment extends to prophylaxis as well as the treatment of established diseases or symptoms. It will further be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.001 mg/kg to about 100 mg/kg per day. The desired dose may conveniently be presented in a single dose or as divided doses administered at appropriate intervals, for example as two, three, four or more subdoses per day.

The present invention also provides for novel pharmaceutical compositions of the compounds of Formula (I). While it is possible that compounds of the present invention may be therapeutically administered as the raw chemical, it is preferable to present the active ingredient as a pharmaceutical formulation. Accordingly, the present invention further provides for pharmaceutical formulations comprising a compound of Formula (I) or a pharmaceutically acceptable salt thereof together with one or more pharmaceutically acceptable carriers and, optionally, other therapeutic and/or prophylactic ingredients. The carrier(s) must be "acceptable" in the sense of being compatible with the other ingredients of the formulation and not deleterious to the recipient thereof.

Formulations of the present invention may be administered in standard manner for the treatment of the indicated diseases, such as orally, parenterally, sublingually, transdermally, rectally, via inhalation or via buccal administration. For buccal administration, the composition may take the form of tablets or lozenges formulated in conventional manner. For example, tablets and capsules for oral administration may contain conventional excipients such as binding agents, (for example, syrup, accacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulphate. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid.

Such preparations may also be formulated as suppositories, e.g., containing conventional suppository bases such as cocoa butter or other glycerides. Compositions for inhalation can be typically provided in the form of a solution, suspension or emulsion that may be administered as a dry powder or in the form of an aerosol using a conventional propellant such as dichlorodifluoromethane or trichlorofluoromethane. Typical transdermal formulations comprise a conventional aqueous or non-aqueous vehicles, such as creams, ointments, lotions or pastes or are in the form of a medicated plaster, patch or membrane.

Additionally, compositions the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The composition according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The biological activity of the compounds of Formula (I) was evaluated according to the following protocols with the appropriate resulting data being provided hereinbelow. In particular, the compounds of Formula (I) may be evaluated for their osteoprotective activity and their anti-uterotrophic profiles using the methods set forth in the following protocols.

Those skilled in the art will appreciate that several acceptable varieties of rat estrogen receptor binding assays are known and available for initial screening of the compounds of the present invention with respect to their ability to bind to the appropriate receptor. Compounds were initially evaluated as set forth below in an rat estrogen receptor binding assay for the ability to inhibit the binding of [$^3$H]-estradiol. Compounds that displayed an $IC_{50}$<10 μM were progressed to an in vitro functional assay of estrogenic activity in the Ishikawa human endometrioma cell line as set forth below.

Subconfluent Ishikawa-Var I cells were removed from maintenance growth conditions and resuspended in phenol red-free DMEM-F12 containing 5% charcoal stripped FBS and 2 mM glutamine at a concentration of 58,500 cells/mL. Cells were plated at a density of 13,000 cells/cm$^2$ and placed in an incubator (37° C., 5% $CO_2$) for 3 days. Cells were harvested and resuspended in phenol red-free DMEM-F12 containing 1% charcoal stripped FBS, 2 mM glutamine, 100 Units/mL penicillin and 100 μg/mL streptomycin to a concentration of 83,000 cells/mL. Cells were seeded at a density of 8300 cells/well in 96 well plates and allowed to attach overnight. Appropriate drug treatments at 2 X concentrations were added in 0.1 mL of medium containing 0.2% DMSO. Plates were incubated for 2 days, media was aspirated and plates washed once with 300 μL 0.9% sterile saline. Plates were frozen at −70° C. and then warmed to RT. The attached cells were assayed for alkaline phosphatase activity by addition of 200 μL of 5 mM p-nitrophenylphosphate in 1 M diethanolamine, pH 10.4, containing 0.1% (w/v) Triton X-100, incubation at 37° C. for 30 min and measurement of absorbance at 405 nm on a Molecular Devices ThermoMax plate reader.

The compounds of the present invention were assayed as set forth above in order to evaluate their ability to induce expression of alkaline phosphatase, an in vitro response specific to estrogen agonists that has been shown to correlate with the in vivo uterotrophic response of estrogen agonists in rats. Referring to Table 1 below, results were expressed as the concentration of various representative compounds of the present invention that induced 50% of their maximal alkaline phosphatase activity ($E_{max}$), with this maximal activity expressed as a percentage of the alkaline phosphatase activity induced by a saturating concentation of estradiol. In additional studies it was shown that all compounds whose $E_{max}$ was<20% functioned as antagonists of estradiol at concentrations that mirrored their receptor binding affinities.

TABLE 1

| | Estrogen Agonist Activity | |
|---|---|---|
| Cmpd no. | $EC_{50}$ (nM)[b] | $E_{max}$ (%)[c] |
| Estradiol | 0.01 | 100 |
| Tamoxifen | 33 | 16.5 ± 0.6 |
| 1 | 2.3 | 11.9 ± 1.2 |
| 3 | 4.9 | 15.7 ± 1.8 |
| 4 | 20 | 18.8 ± 2.3 |
| 5 | 7.3 | 15.0 ± 3.0 |

TABLE 1-continued

| | Estrogen Agonist Activity | |
|---|---|---|
| Cmpd no. | $EC_{50}$ (nM)[b] | $E_{max}$ (%)[c] |
| 9 | 58 | 3.8 ± 0.9 |
| 10 | 6.9 | 14.8 ± 2.4 |
| 11 | 11 | 14.0 ± 1.5 |
| 12 | 70 | 19.4 ± 2.0 |
| 13 | 4.6 | 16.5 ± 1.7 |
| 14 | 12 | 6.3 ± 1.2 |
| 15 | 8.6 | 8.9 ± 1.4 |
| 16 | 18 | 11.8 ± 1.9 |
| 21 | 6.9 | 18.8 ± 2.6 |
| 22 | 17 | 15.3 ± 2.4 |

Compound No. 1 was found to bind to the estrogen receptor with approx. 10 fold higher affinity than tamoxifen which translated to a lower $EC_{50}$ in the Ishikawa cell function assay (see Table 1). In addition, Compound No. 1 possessed significantly lower agonist activity ($E_{max}$) than tamoxifen. A series of amide analogs of Compound No. 1 were evaluated to establish the structural requirements to lower the $EC_{50}$ and to minimize $E_{max}$ in the Ishikawa cell functional assay. The data showed that a wide range of structural diversity (lipophilicity, steric bulk, H-bond donors and acceptors) was tolerated in this region of the molecule, and only the bulky Compound No. 12 showed reduced receptor affinity. Compound No. 1 showed the highest affinity in the receptor binding assay and possessed the lowest $EC_{50}$ functional assay, however when $E_{max}$ data was analyzed, Compound Nos. 9, 14 and 15 showed the lowest residual agonist activity.

Figure 1:
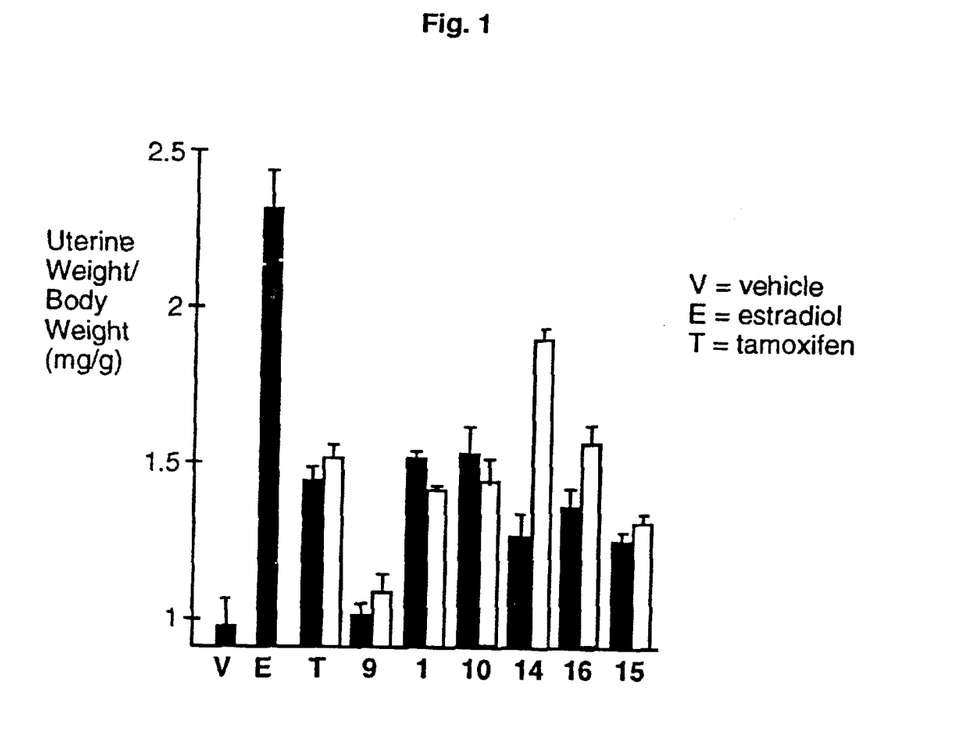
FIG. 1 sets forth data representative of the uterotrophic activity of the compounds of the present invention in immature rats.

In order to evaluate the compounds set forth above for in-vivo anti-uterotrophic activity, groups of five 21 day old female SD rats (30–35g) were weighed and the average weights recorded for each treatment group as illustrated in FIG. 1. Stock solutions (10 X) of the triphenylethylene analogs in ethanol were diluted with 0.5% methyl cellulose and 10 μmol/kg was dosed by gavage to the animals. Estradiol was dissolved in sesame oil and 100 nmol/kg dosed by subcutaneous injection. Animals were dosed for 3 days and sacrificed on day 4 by $CO_2$ asphyxiation. The body weights were obtained, uteri removed, blotted and weighed. Data is expressed as uterine weight/body weight±standard error. Solid bars represent data from animals dosed with test compound alone. Open bars represent data from animals dosed with test compounds 6 h prior to a dose of estradiol. Compounds 9 and 15 showed less residual agonist activity than tamoxifen.

As an example of the functional profile of these compounds in bone, Compound No. 9 was evaluated in 90 day old estrogen deficient ovariectomized rats for their ability to inhibit loss of bone mineral density. Ninety day old SD rats were divided into groups of six. Three groups were surgically ovariectomized. Two days post-ovariectomy, animals were dosed by gavage with either 10 μmol/kg of Compound No. 9 in 0.5% methyl cellulose or vehicle once a day for 28 days. One group of aminals was sham-operated, and 2 days post-ovariectomy dosed with vehicle once a day for 28 days. At 0, 14 and 28 days, rats were anesthesized with isoflurane and placed in the supine position with their spines parallel to the long axis of the densitometer table. The lumbar spine was scanned using the pelvic bones as a landmark. To scan the right tibia, the leg was taped in position parallel to the long axis of the table and scanned up to the junction with the femur. Analysis of the lumbar spine was accomplished by dividing vertebra and inter-vertebral spaces with normal analysis software and including only target vertebra in the global region of interest. The right tibia was analysed with subregional high resolution software, focusing on the 3–5 mm distal from the growth plate previously identified as a region of accelerated bone loss due to ovariectomy. Data at 14 and 28 days did not differ significantly. Data at 28 days is shown in FIG. 2.

Figure 2:
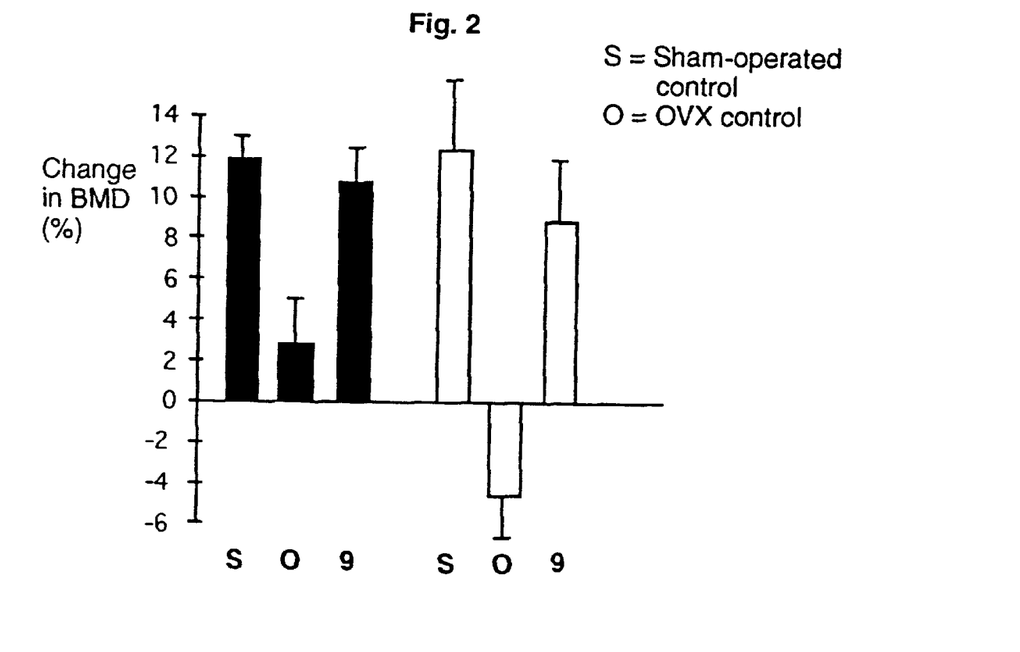
FIG. 2 sets forth data representative of changes in bone mineral density in ovariectomized rats in lumbar spine and tibia.

Referring to FIG. 2, an orally administered dose of 10 μmol/kg of Compound No. 9 demonstrated full agonist activity, maintaining BMD at the levels of the sham-operated rats for the duration of the 28 day study. Biochemical data demonstrated that the mechanism of action was through inhibition of bone resorption consistent with their activity as estrogen agonists in bone. BMD was measured by dual-energy X-ray absorptiometry using a Hologic QDR-2000 bone densitometer using a regional high-resolution software package with default scan length, width, line spacing and point resolution of 2, 0.75, 0.01 and 0.005 in. respectively.

We claim:

1. A compound of Formula I:

(I)

wherein $R^1$ is $-(CH_2)_nCR5=CR^6R^7$; $-(CH_2)_mC(X)NR^8R^9$; or $R^2$ and $R^3$ are independently H, $-CH_3$, $-OH$, $-OCH_3$, $-OCH_2CH_3$ or $-CH_2(CH_3)_2$;

$R^4$ is $-CN$, $-NO_2$, $-CH_3$, $-CH_2CH_3$, $-CH_2CH_2-Y$ or $-Y$;

$R^5$ and $R^6$ are independently H, $-C_{1-4}$alkyl, $-C_{2-4}$alkenyl, $-C_{2-4}$alkynyl, $-X-C_{1-3}$alkyl, $-X-C_{2-4}$alkenyl, $-X-C_{2-4}$alkynyl or $-Y$;

$R^7$ is $-CN$, $-C_{1-4}$alkyl$-OH$, $-C(O)O(CH_3)_3$, $-C(O)NR^{10}R^{11}$, $-C(O)NR^{12}R^{13}$, $-C_{1-4}$alkyl$-NR^{10}R^{11}$, $-C(O)R^{12}$, $-C(O)OR^{12}$, $-C(O)NR^{12}OR^{13}$, $-C(O)NHC(O)R^{12}$, $-C(NH_2)(NOR^{12})$, $-S(O)R^{12}$, $-S(O)(O)(OR^{12})$, $-S(O)(O)(NHCO_2R^{12})$, $PO_3R^{12}$, $-P(O)(NR^{12}R^{13})(NR^{12}R^{13})$, $-P(O)(NR^{12}R^{13})(OR^{14})$, $-CONR^{12}(CH_2)_q$ $OCH_3$, $-CONR^{12}(CH_2)_qNR^8R^9$ or oxadizole substituted with methyl;

$R^8$ and $R^9$ are independently hydrogen, $-C_{1-7}$alkyl, $-C_{3-7}$cycloalkyl, $-O-C_{1-7}$alkyl, $-C_{1-7}$alkyl$-Y$ or phenyl;

$R^{10}$ and $R^{11}$ are independently methyl or ethyl or, taken together form a morpholino group bonded via its nitrogen atom;

$R^{12}$, $R^{13}$ and $R^{14}$ are independently H, $-C_{1-12}$alkyl, $-C_{2-12}$alkenyl, $-C_{2-12}$alkynyl, $-O-C_{1-12}$alkyl, $-O-C_{2-12}$alkenyl, $-O-C_{2-12}$alkynyl, $-C_{3-7}$cycloalkyl, $-C_{3-7}$cycloalkenyl, linear and cyclic heteroalkyl, aryl, heteroaryl or $-Y$;

X is oxygen or sulfur;

Y is a halogen;

n is an integer selected from 0, 1 or 2;

m is the integer 1 or 2;

p is an integer selected from 1 to 4; and q is an integer from 1–12.

2. A compound according to claim 1 wherein X is 0.

3. A compound according to claim 2 wherein $R^1$ is $R^1$ is $-(CH_2)_nCR^5=CR^6R^7$.

4. A compound according to claim 1 wherein $R^2$ and $R^3$ are independently selected from H, $-OH$ or $-OCH_3$.

5. A compound according to claim 4 wherein $R^2$ and $R^3$ are H.

6. A compound according to claim 1 wherein $R^4$ is either $-CH_3$, $-CH_2CH_3$ or $-CH_2CH_2-Cl$.

7. A compound according to claim 1 wherein $R^5$ and $R^6$ are independently H or $-C_{1-4}$alkyl.

8. A compound according to claim 1 wherein $R^8$ and $R^9$ are independently hydrogen, $-C_{1-7}$alkyl or $-C_{3-7}$cycloalkyl.

9. A compound according to claim 3 wherein $R^7$ is $CO(O)O(CH_3)_3)$ $-C(O)NR^{10}R^{11}$, $-C(O)NR^{12}R^{13}$, $-C(O)OR^{12}$, $-C(O)NHC(O)R^{12}$, $-C(NH_2)(NOR^{12})$, $-S(O)(O)(NHCO_2R^{12})$, $PO_3R^{12}$, $-P(O)(NR^{12}R^{13})(NR^{12}R^{13})$ or $P(O)(NR^{12}R^{13})(OR^{14})$.

10. A compound according to claim 1 wherein $R^{12}$, $R^{13}$ and $R^{14}$ are independently H, $-C_{1-12}$alkyl, $-C_{2-12}$alkenyl.

11. A compound according to claim 1 wherein the compound is selected from one of the following:

3-[4-(1,2-Diphenyl-but-1-enyl)-phenyl]—N,N-diethyl acrylamide;

3-[4-(1,2-Diphenyl-but-1-enyl)-phenyl]-N,N-diethyl propionamide;

2-[4-(1,2-Diphenyl-but-1-enyl)-phenyl] cyclopropanecarboxylic acid diethylamide;

3-[4-(1,2-Diphenyl-but-1-enyl)-phenyl]—N,N-diethyl-2-methyl-acrylamide;

3-[4-(1,2-Diphenyl-but-1-enyl-phenyl]-but-2-enoic acid diethylamide;

3-[4-(1,2-Diphenyl-but-1-enyl)-phenyl]-acrylic acid methyl ester;

3-[4-(1,2-Diphenyl-but-1-enyl)-phenyl]-acrylonitrile;

3-[4-(1,2-Diphenyl-but-1-enyl)-phenyl]-acrylic acid tert-butyl ester;

3-[4-(1,2-Diphenyl-but-1-enyl)-phenyl]-acrylic acid;

3-[4-(1,2-Diphenyl-but-1-enyl)-phenyl]-1-morpholin-4-yl-prop-2en-1-one;

3-[4-(1,2-Diphenyl-but-1-enyl)-phenyl]-N-(3-methoxypropyl)-acrylamide;

N,N-Dicyclohexyl-3-[4-(1,2diphenyl-but-1-enyl)-phenyl] acrylamide;

N-(2-Dimethylamino-ethyl)-3-[4-(1,2-diphenyl-but-1-enyl)phenyl]-N-ethyl acrylamide;

3-[4-(1,2-Diphenyl-but-1-enyl)-phenyl]-N-methyl-N-octyl acrylamide;

3-[4-(1,2-Diphenyl-but-1-enyl)-phenyl] acrylamide;

3-[4-(1,2-Diphenyl-but-1-enyl)-phenyl]—N-ethyl acrylamide;

1-Amino-3-[4-(1,2-diphenyl-but-1-enyl)phenyl]-prop-2-ene-1-one oxime;

3-{2-[4-(1,2-Diphenyl-but-1-enyl)-phenyl]-vinyl}-5-methyl-[1,2,4]-oxadiazole;

3-[4-(1,2-Diphenyl-but-1-enyl)-phenyl]-prop-2-ene-1-ol;

{3-[4-(1,2-Diphenyl-but-1-enyl)-phenyl]-allyl}-dimethylamine;

3-[4-(1,2-Diphenyl-but-1-enyl)-phenyl]-N,N-diethyl thioacrylamide; or

3-[4-(1,2-Diphenyl-but-1-enyl)-phenyl]-N-(3hydroxy-propyl)-acrylamide.

12. A method of treating a mammal for osteoporosis comprising administering to a mammal in need of said treatment an effective amount of a compound according to claim 1.

13. A method of treating a mammal for arthritic disease which comprises administering to a mammal in need of said treatment an effective amount of a compound according to claim 1.

14. A method of treating a mammal for breast cancer which comprises administering to a mammal in need of said treatment an effective amount of a compound according to claim 1.

15. A method of treating a mammal for cardiovascular disease which comprises administering to a mammal in need of said treatment an effective amount of a compound according to claim 1.

16. A method of preventing osteoporosis in a mammal comprising administering to a mammal in need of said prevention an effective amount of a compound according to claim 1.

17. A method of preventing arthritic disease in a mammal which comprises administering to a mammal in need of said prevention an effective amount of a compound according to claim 1.

18. A method of preventing breast cancer in a mammal which comprises administering to a mammal in need of said prevention an effective amount of a compound according to claim 1.

19. A method of preventing cardiovascular disease in a mammal which comprises administering to a mammal in need of said prevention an effective amount of a compound according to claim 1.

* * * * *